United States Patent [19]
Cormack et al.

[11] Patent Number: 6,090,919
[45] Date of Patent: Jul. 18, 2000

[54] FACS-OPTIMIZED MUTANTS OF THE GREEN FLUORESCENT PROTEIN (GFP)

[75] Inventors: Brendan P. Cormack, Santa Cruz; Raphael H. Valdivia, Palo Alto; Stanley Falkow, Portola Valley, all of Calif.

[73] Assignee: The Board of Trustees of the Leland Stanford Junior University, Palo Alto, Calif.

[21] Appl. No.: 09/135,418

[22] Filed: Aug. 17, 1998

Related U.S. Application Data

[62] Division of application No. 08/791,332, Jan. 31, 1997, Pat. No. 5,804,387.
[60] Provisional application No. 60/010,960, Feb. 1, 1996.

[51] Int. Cl.$^7$ .............................. C07K 1/00; C07H 21/02
[52] U.S. Cl. .............................................................. 530/350
[58] Field of Search ............................ 530/350; 536/23.1

[56] References Cited

U.S. PATENT DOCUMENTS

| | | | |
|---|---|---|---|
| 5,162,227 | 11/1992 | Cormier | 435/252.33 |
| 5,360,728 | 11/1994 | Prahser | 435/189 |
| 5,422,266 | 6/1995 | Cormier et al. | 435/252.3 |
| 5,491,084 | 2/1996 | Chalfie et al. | 435/189 |
| 5,541,309 | 7/1996 | Prasher | 536/23.2 |
| 5,625,048 | 4/1997 | Tsien et al. | 536/23.4 |

FOREIGN PATENT DOCUMENTS

| | | |
|---|---|---|
| 96/23810 | 8/1996 | WIPO . |
| 96/27675 | 9/1996 | WIPO . |
| 97/11094 | 3/1997 | WIPO . |

OTHER PUBLICATIONS

Delagrave et al. (1995) Red–shifted excitation mutants of the green fluorescent protein. Bio/Technology 13: 151–154, Feb. 1995.

Cormack et al., "Regional Codon Randomization: Defining A TATA–Binding Surface Required for RNA Polymerase III Transcription," *Science* (1993) vol. 262:243–248.

Cormack, et al., "FACS–Optimized Mutants Of The Green Fluorescent Protein (GFP)," *Gene* (Jul. 1996) vol. 173:33–38.

Chalfie, et al., "Green Fluorescent Protein As A Marker For Gene Expression," *Science* (Feb. 11, 1994) vol. 263:802–804.

Cubitt, et al., "Understanding, Improving And Using Green Fluorescent Proteins," *TIBS* (Nov. 1995) vol. 20:448–455.

Davis, et al., "A Nuclear GFP That Marks Nuclei In Living Drosophila Embryos: Maternal Supply Overcomes A Delay In The Appearance Of Zygotic Fluorescence," *Dev. Bio.* (1995) vol. 170:726–729.

Delgrave, et al., "Red–Shifted Excitation Mutants Of The Green Fluorescent Protein," *Bio. Technology* (Feb. 1995) vol. 13:151–154.

Glaser, et al., "Antibody Engineering By Codon–Based Mutagenesis In A Filamentous Phage Vector System," *J. of Immunology* (Dec. 1992) vol. 149, No.(12):3903–3913.

Haas, et al., "Codon Usage Limitation In The Expression Of HIV–1 Envelope Glycoprotein," *Current Biology* (1996) vol. 6, No. (3):315–324.

Heim, et al., "Wavelength Mutations And Posttranslational Autoxidation Of Green Fluorescent Protein," *Proc. Nat'l Acad. Sci USA* (1994) 12501–12504.

Helm, et al., "Improved Green Fluorescence," *Nature* (1995) vol. 373:663–664.

Hu, et al., "Expression of Aequorea Green Flourescent Protein In Plant Cells," *FEBS Letters* (1995) vol. 369:331–334.

Inouye, et al., "Aequorea Green Fluorescent Protein: Expression Of The Gene And Fluorescence Characteristics Of The Recombinant Protein," *FEBS Letters* (Jan.1994) vol. 341:277–280.

Kaether, et al., "Visualization Of Protein Transport Along The Secretory Pathway Using Flourescent Protein," *FEBS Letters* (1995) vol. 369:267–271.

Morise, et al., "Intermolecular Energy Transfer In The Bioluminescence System Of Aequorea," *Biochemistry* (1974) vol. 13, No. (12):2656–2662.

Olson, et al., "Analysis of MAP 4 Function In Living Cells Using Green Fluorescent Protein (GFP) Chimeras," *J. Of Cell Bio.* (1995) vol. 5, 130:639–650.

Rizzuto, et al., "Chimeric Green Fluorescent Protein As A Tool For Visualizing Subcellular Organelles In Living Cells," *Current. Bio.* (1995) vol. 5, No. (6):635–642.

Ward, et al., "Spectrophotomeric Identity Of The Energy Transfer Chromophores In Renilla And Aequorea Green Fluorescent Proteins," *Photochem. And Photobio.* (1980) vol. 31:611–615.

Yang, et al., "Dual Color Microscopic Imagery Of Cells Expressing The Green Fluorescent Protein And A Red––Shifted Variant," *Gene* (Jul. 1996) vol. 173:19–23.

Zolotukhin, et al., "A Humanized Green Fluorescent Protein cDNA Adapted For High–Level Expression In Mammalian Cells," *J. Virology* (Jul. 1996) vol. 70:4646–4654.

*Primary Examiner*—Rebecca E. Prouty
*Assistant Examiner*—Einar Stole
*Attorney, Agent, or Firm*—Bozicevic, Field & Francis; Pamela Sherwood

[57] ABSTRACT

Three classes of GFP mutants having single excitation maxima around 488 nm are brighter than wild-type GFP following 488 nm excitation. GFPmut1 has a double substitution: F64L, S65T; GFPmut2 has a triple substitution: S65A, V68L, S72A; and GFPmut3 is characterized by the double substitution S65G, S72A. The excitation maxima of the three mutants are at 488 nm, 481 nm and 501 nm respectively. The fluorescence intensities following excitation at 488 nm are an order of magnitude higher than that of wild-type GFP excited at 488 nm in *E. coli*. The expression of GFP is observable minutes after induction.

15 Claims, 5 Drawing Sheets

FIG. 3-A
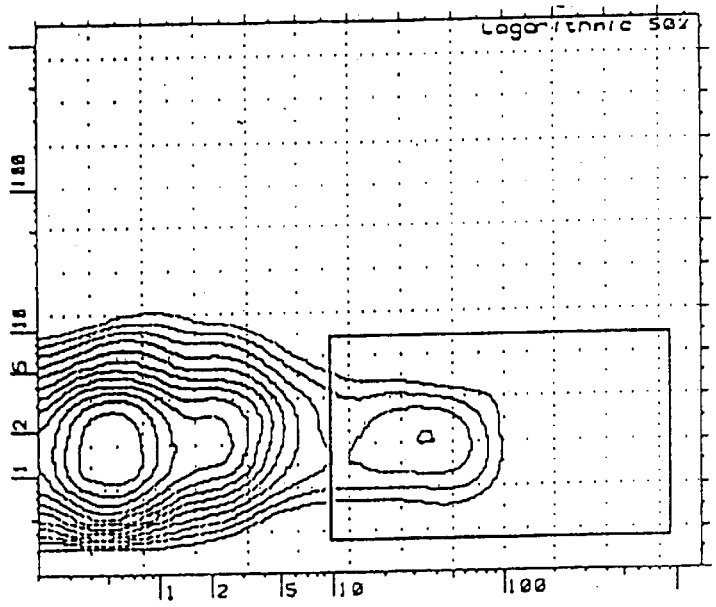
Fluorescence Intensity (log scale) with 488 nm excitation
Emission read with 510/40 bandpass filter
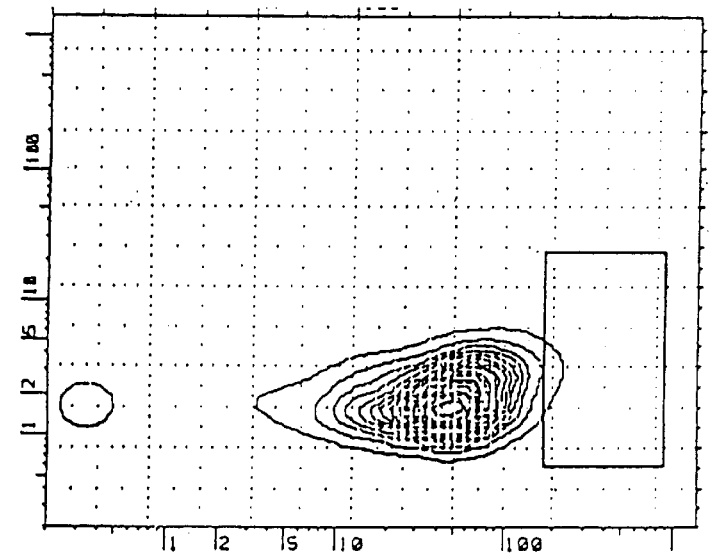
FIG. 3-B
Fluorescence Intensity (log scale) with 488 nm excitation
Emission read with 510/40 bandpass filter

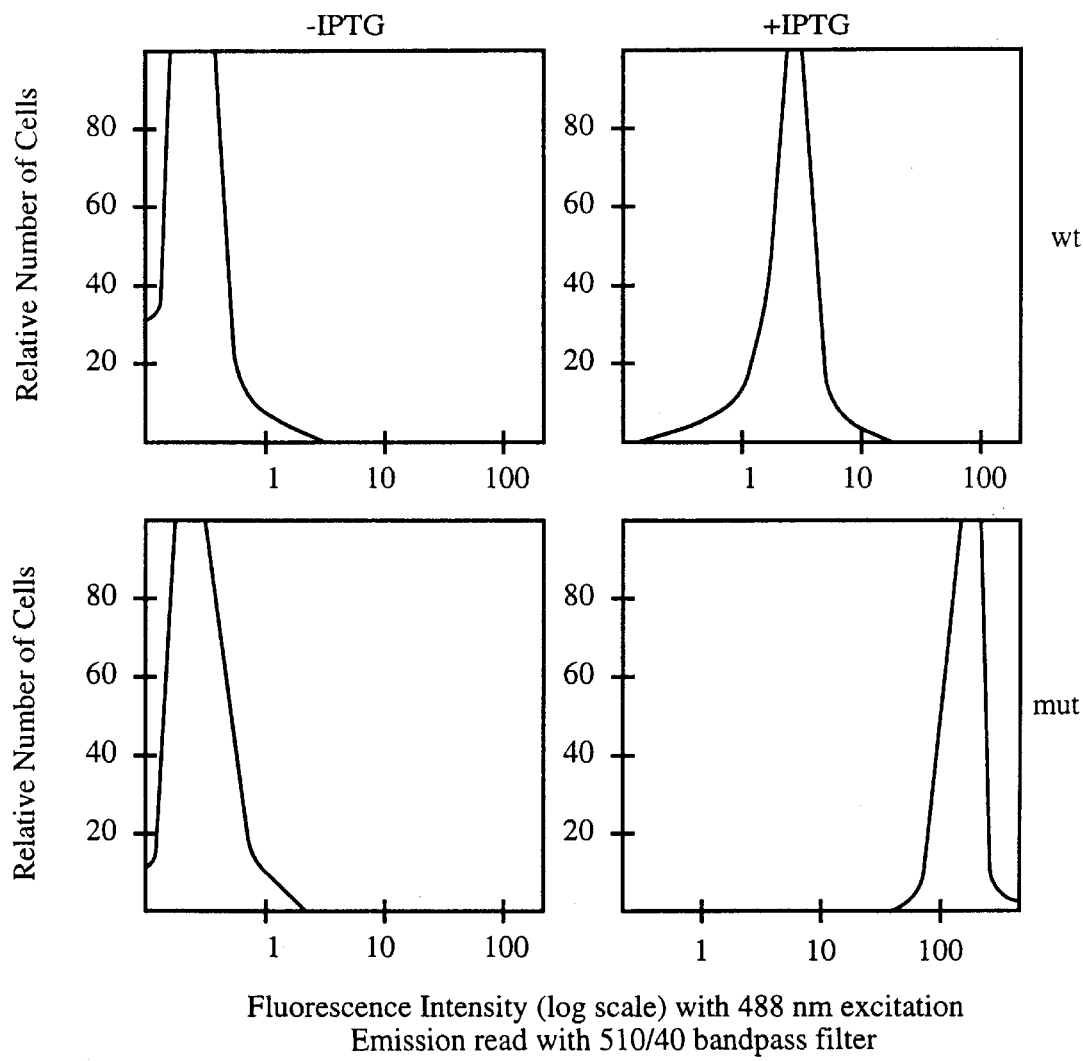
FIG. 3-C

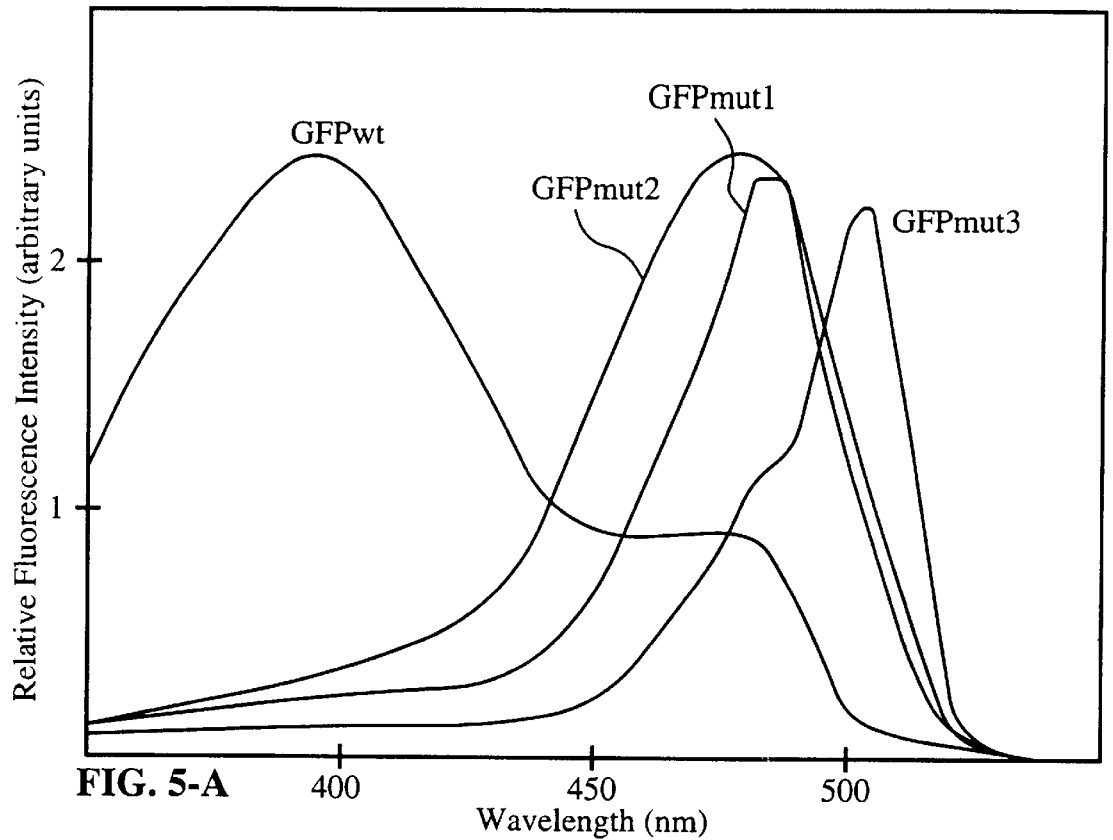
FIG. 5-A
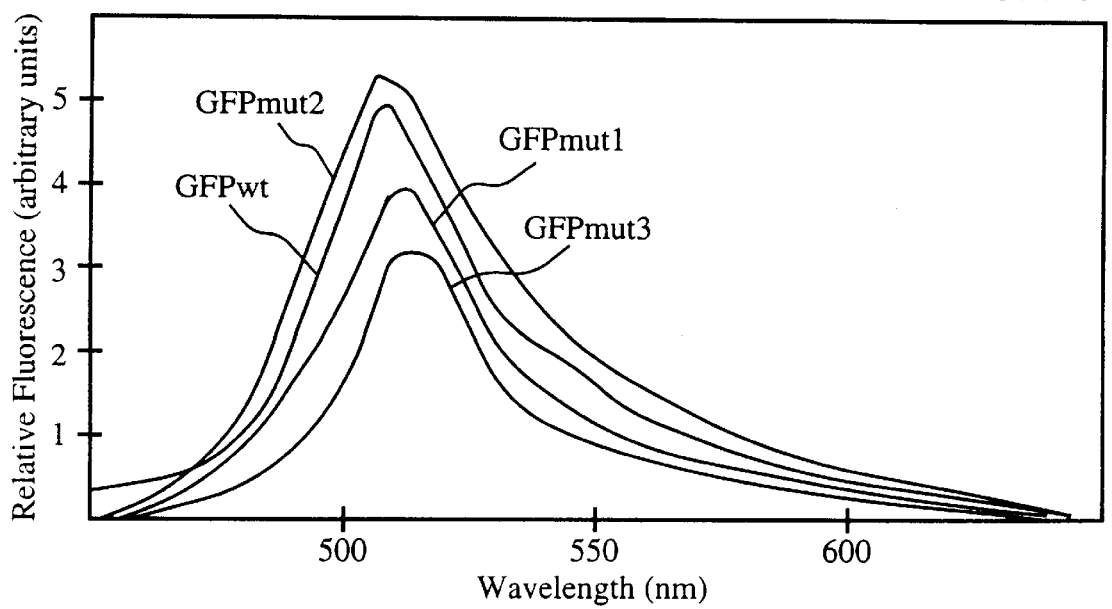
FIG. 5-B

```
                         SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ix) FEATURE:
        (A) NAME/KEY: GFPmut1 fragment (xi) SEQUENCE DESCRIPTION:  SEQ ID NO: 1:

Leu Thr Tyr Gly Val Gln Cys Phe Ser
1               5

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ix) FEATURE:
        (A) NAME/KEY: GFPmut2 fragment (xi) SEQUENCE DESCRIPTION:  SEQ ID NO: 2:

Phe Ala Tyr Gly Leu Gln Cys Phe Ala
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ix) FEATURE:
        (A) NAME/KEY: GFPmut3 fragment (xi) SEQUENCE DESCRIPTION:  SEQ ID NO: 3:

Phe Gly Tyr Gly Val Gln Cys Phe Ala
1               5

(2) INFORMATION FOR SEQ ID NO:4:
```

```
        (i) SEQUENCE CHARACTERISTICS:
            (A) LENGTH: 27 base pairs
            (B) TYPE: nucleic acid
            (C) STRANDEDNESS: double stranded
            (D) TOPOLOGY: linear (ix) FEATURE:
            (A) NAME/KEY: wild-type GFP fragment (xi) SEQUENCE DESCRIPTION:  SEQ ID NO: 4:

TTC TCT TAT GGT GTT CAA TGC TTT TCA                                   27
Phe Ser Tyr Gly Val Gln Cys Phe Ser
1               5

(2) INFORMATION FOR SEQ ID NO:5:

(i) SEQUENCE CHARACTERISTICS:
            (A) LENGTH: 46 base pairs
            (B) TYPE: nucleic acid
            (C) STRANDEDNESS: single stranded
            (D) TOPOLOGY: linear (ix) FEATURE:
            (A) NAME/KEY: GF1
            (D) OTHER INFORMATION: primer for PCR containing ribosome
                binding site of phage T7 gene10.

(xi) SEQUENCE DESCRIPTION:  SEQ ID NO: 5:

GATTTCTAGA TTTAAGAAGG AGATATACAT ATGAGTAAAG GAGAAG                     46

(2) INFORMATION FOR SEQ ID NO:6:

(i) SEQUENCE CHARACTERISTICS:
            (A) LENGTH: 100 base pairs
            (B) TYPE: nucleic acid
            (C) STRANDEDNESS: single stranded
            (D) TOPOLOGY: linear (ix) FEATURE:
            (A) NAME/KEY: GF2
            (D) OTHER INFORMATION: primer for PCR containing mutagenized
                region (template strand).

(xi) SEQUENCE DESCRIPTION:  SEQ ID NO: 6:

TGCTGTTTCA TAAGATCTGG GTATCTTGAA                                      30

AAGCATTGAA CACCATAAGA GAAAGTAGTG                                      60

ACAAGTGTTG GCCATGGAAC AGGTAGTTTT                                      90

CCAGTAGTGC                                                           100
```

FACS-OPTIMIZED MUTANTS OF THE GREEN FLUORESCENT PROTEIN (GFP)

RELATED APPLICATION DATA

This application is a divisional of patent application Ser. No. 08/791,332, filed on Jan. 31, 1997, now U.S. Pat. No. 5,804,387 which claims the benefit of U.S. Provisional Patent Application No. 60/010,960, filed Feb. 1, 1996, herein incorporated by reference.

This invention was made with U.S. Government support under grant No. AI 36396, awarded by the National Institutes of Health. The U.S. Government has certain rights in this invention.

FIELD OF THE INVENTION

The present invention relates to the field of genetic engineering, and in particular to green fluorescent protein (GFP) mutants having FACS-optimized spectra.

BACKGROUND OF THE INVENTION

Fluorescence labeling is a particularly useful tool for marking a protein or cell of interest. Traditionally, a protein of interest is purified and then covalently conjugated to a fluorophore derivative. For in vivo studies, the protein-dye complex is then inserted into the cells of interest using micropipetting or a method of reversible permeabilization. The dye attachment and insertion steps, however, make the process laborious and difficult to control.

Another way of labeling a protein of interest is to concatenate the gene expressing the protein of interest and a gene expressing a marker, and then express the fusion product. Typical markers include β-galactosidase, firefly luciferase and bacterial luciferase. These markers, however, require exogenous substrates or cofactors and are therefore of limited use for in vivo studies.

A marker that does not require any exogenous cofactor or substrate is the green fluorescent protein (GFP) of the jellyfish *Aequorea victoria*, a protein with an excitation maximum at 395 nm and an emission maximum at 510 nm. Uses of GFP for the study of gene expression and protein localization are discussed in more detail in papers by Chalfie et al. in *Science* 263 (1994), p. 802–805, and Heim et al. in *Proc. Nat. Acad. Sci.* 91 (1994), p. 12501–12504. Some properties of wild-type GFP are disclosed for example in papers by Morise et al. in *Biochemistry* 13 (1974), p. 2656–2662, and Ward et al. in *Photochem. Photobiol.* 31 (1980), p. 611–615. An article by Rizzuto et al. in *Curr. Biology* 5 (1995), p. 635–642 discusses the use of wild-type GFP as a tool for visualizing subcellular organelles in cells, while a paper by Kaether and Gerdes in *Febs Letters* 369 (1995), p. 267–271, reports the visualization of protein transport along the secretory pathway using wild-type GFP. The expression of GFP in plant cells is discussed in an article by Hu and Cheng in *Febs Letters* 369 (1995), p. 331–334, while GFP expression in Drosophila embryos is described in a paper by Davis et al. in *Dev. Biology* 170 (1995), p. 726–729.

GFP is a 238-amino acid protein, with amino-acids 65–67 involved in the formation of the chromophore. A biosynthetic scheme for the chromophore is proposed in the above-mentioned article by Heim et al. (1994), and is shown in FIG. 1. Some of the newly translated protein precipitates as non-fluorescent inclusion bodies. For the protein that does not precipitate, amino acids 65–67 may be involved in cyclization and oxidation to form the chromophore. The time constant for chromophore formation was observed (Heim et al., 1995) to be on the order of two hours, suggesting that wild-type GFP would not be a practical marker for monitoring fast changes in gene expression.

Wild-type GFP has a major excitation peak at 395 nm and a minor excitation peak at 470 nm. The absorption peak at 470 nm allows the monitoring of GFP levels using standard fluorescein isothiocyanate (FITC) filter sets and the 488 nm line of an Ar ion laser. The ability to excite GFP at 488 nm also permits the use of GFP with standard fluorescence activated cell sorting (FACS) equipment. The emission levels of wild-type GFP excited at 488 nm are relatively low, however, and the resulting low signal-to-noise ratio and limited dynamic range limit the use of GFP with typical FACS equipment. Mutations in GFP leading to brighter emission following 488 nm excitation would be of value in many applications, including FACS.

Mutations in GFP which shift the excitation maximum from 395 nm to about 490 nm have been reported by Delagrave et al. in *Biotechnology* 13 (1995), p. 151–154, and Heim et al. in *Nature* 373 (1995), p. 663–664. The above-mentioned articles by Delagrave et al. and Heim et al. (1995) are herein incorporated by reference. Mutants with Ala, Gly, Ile, Cys or Thr substituted for Ser65 had large shifts in excitation maxima, and fluoresced more intensely than wild-type protein when excited at 488 nm. Other mutants with altered spectra are disclosed in the previously-mentioned paper by Heim et al. (1994). A summary of the characteristics of the mutants disclosed in the two Heim et al. papers (1994 and 1995) is given in Table 1:

TABLE 1

| Mutation | Excitation maximum | Emission maximum | Relative fluorescence (%) |
| --- | --- | --- | --- |
| None | 396 nm | 508 nm | =100 |
| Ser-202 to Phe Thr-203 to Ile | 398 nm | 511 nm | 117 (w/ 395 nm exc) |
| Ile-167 to Val | 471 nm | 502 nm | 166 (w/ 475 nm exc) |
| Ile-167 to Thr | 471 nm | 502 nm | 188 (w/ 475 nm exc) |
| Tyr-66 to His | 382 nm | 448 nm | 57 (w/ 395 nm exc) |
| Tyr-66 to Trp | 458 nm | 480 nm | Not done |
| Ser-65 to Thr | 489 nm | 511 nm | ~600 |
| Ser-65 to Cys | 479 nm | 507 nm | ~600 |

The mutation of Ser65 to Thr or Cys was observed to increase by a factor of 6 the fluorescence of GFP following 488 nm excitation. However, further improvement in the fluorescence intensity of GFP excited at 488 nm would clearly be desirable.

OBJECTS AND ADVANTAGES OF THE INVENTION

It is a primary object of this invention to provide GFP mutants with increased fluorescence following excitation at 488 nm. It is another object of this invention to provide GFP mutants that allow the monitoring of GFP production minutes after induction of GFP expression. It is yet another object of the present invention to provide target positions for mutagenesis schemes aimed at generating brighter and more soluble GFP mutants. It is a further object of this invention to provide starting mutations to be used in conjuction with further changes/mutations to generate improved mutant GFPs. These and other objects and advantages will become more apparent after consideration of the ensuing description and the accompanying drawings.

SUMMARY OF THE INVENTION

The present invention provides a cell comprising a nucleic acid encoding an improved mutant green fluorescent protein.

A set of mutation positions of the mutant GFP comprises at least one of position 64, 68 or 72. The set of positions further comprises a second position, preferably position 65. The set of positions consists of all amino acid positions in the mutant GFP at which an amino acid differs from the corresponding amino acid of wild-type GFP.

A set of mutations of the mutant protein comprises a first mutation selected from F64L, V68L, and S72A. Preferably, the set of mutations further comprises a second mutation selected from S65T, S65A and S65G. The set of mutations consists of all mutations in the mutant protein, relative to wild-type GFP. In one embodiment, the set of mutations consists essentially of F64L and S65T. In another embodiment, the set of mutations consists essentially of V68L, S72A and S65A. In still another embodiment, the set of mutations consists of S72A and S65G.

The set of mutations preferably comprises at least two mutations within a target mutagenesis region containing the chromophore. The target mutagenesis region consists substantially of a sequence of less than 20 amino acids. In one embodiment, the set of mutations consists essentially of two mutations.

In particular embodiments, the set of mutations comprises a subset selected from (F64L,S65T), (S65A,V68L,S72A) and (S65G, S72A). Preferably, the set of mutations consists essentially of one of the subsets. In three different embodiments of the present invention, amino acid sequences containing the GFP chromophore comprise LTYGVQCFS (SEQ ID NO; 1), FAYGLQCFA (SEQ ID NO: 2) or FGYGVQCFA (SEQ ID NO: 3), respectively.

A 488-nm-excited fluorescence signal from the mutant protein is higher than a 488-nm-excited fluorescence signal from wtGFP expressed under similar conditions (similar promoter, cell, temperature, etc.). Mutants GFP of the present invention are significantly brighter than wtGFP particularly at high temperatures (e.g. 37° C.), in part because of the better folding properties of the mutants at high temperatures. In particular, the solubility of mutants of the present invention is significantly higher than the solubility of wtGFP in cells grown at 37° C.

The present invention provides mutants with single excitation peaks substantially at 490 nm or 500 nm, and emission peaks substantially at 510 nm. The mutants' excitation spectra are optimized for excitation using the 488 nm line of Ar ion lasers used in typical FACS equipment.

Bacterial, plant, yeast and mammalian cells are suitable for use with mutants of the present invention. The nucleic acid comprises a regulatory element (e.g. promoter, repressor, enhancer) operatively connected to a coding portion encoding a mutant GFP. At least some of the codons of the nucleic acid are optimized for expression in the particular type of cell under analysis. The nucleic acid is either part of a plasmid or integrated at a chromosomal location in a chromosome of the cell.

The present invention further provides a method of analyzing a cell. The method comprises the steps of expressing a nucleic acid encoding a mutant GFP of the present invention, and measuring a fluorescence signal from the mutant GFP. The cell is sorted by fluorescence activated cell sorting according to the signal. The cell is preferably illuminated at a wavelength substantially equal to 490 nm. The signal is measured at least at an emission wavelength substantially equal to 510 nm. That is, the spectrum of the emission filter used for measuring the signal has a substantial component (preferably, within the full-width-at-half-maximum of the filter spectrum) at 510 nm.

In one application the nucleic acid comprises a gene of interest encoding a protein of interest. The protein of interest is distinct from the mutant GFP encoded by the nucleic acid. The fluorescence signal from the cell then indicates the presence of the gene of interest in the cell. In another application, the cell comprises a protein of interest fused to a mutant GFP of the present invention. Identifying the intracellular location of the mutant GFP than allows identifying the intracellular location of the protein of interest. In yet another application, a regulatory element operatively connected to a coding portion encoding a mutant GFP is exposed to an environmental stimulus. The fluorescence signal from the cell then measures the effect of the stimulus on the activity of the regulatory element. Suitable stimuli include compounds of interest (e.g. drugs), temperature, acidity, and species-specific factors. Species-specific factors are understood to comprise factors unique to a particular species; exposing a regulatory element to a species-specific factor is preferably accomplished by introducing the regulatory element into a cell of the target species.

In a particularly useful application, a library of promoters is exposed to a first environmental stimulus. Each promoter is connected to a mutant GFP of the present invention. A first pattern characterizing the effect of the first stimulus on the library is generated by measuring fluorescence signals corresponding to each promoter in the library. Comparing the first pattern to a second pattern corresponding to a known second stimulus can provide information on the similarity of the modes of action of the two stimuli.

In yet another application, a mutant of the present invention is paired within the same cell with an additional GFP spectrally distinguishable from the mutant. An additional fluorescence signal from the additional GFP is measured independently from the signal from the mutant GFP. The additional GFP preferably comprises a GFP variant with an excitation peak lower than 450 nm and with low excitability at 490 nm.

DESCRIPTION OF THE FIGURES

FIG. 3-A shows the results of a FACS scan of a total library of mutants 2.5 hours after induction.

FIG. 3-B shows the results of a FACS scan of a high-fluorescing subpopulation of mutants.

FIG. 3-C shows fluorescence intensities of a mutant and wild-type GFP excited at 488 nm, with and without inducer.

FIG. 5-A shows excitation spectra of wild-type GFP and three mutant classes of the present invention, with emission recorded at 540 nm.

FIG. 5-B shows emission spectra of wild-type GFP and of the three mutant classes analyzed in FIG. 5-A, recorded with excitation wavelengths of 395 nm for wild-type GFP and 450 nm for the mutant proteins.

DETAILED DESCRIPTION

Figure 1:
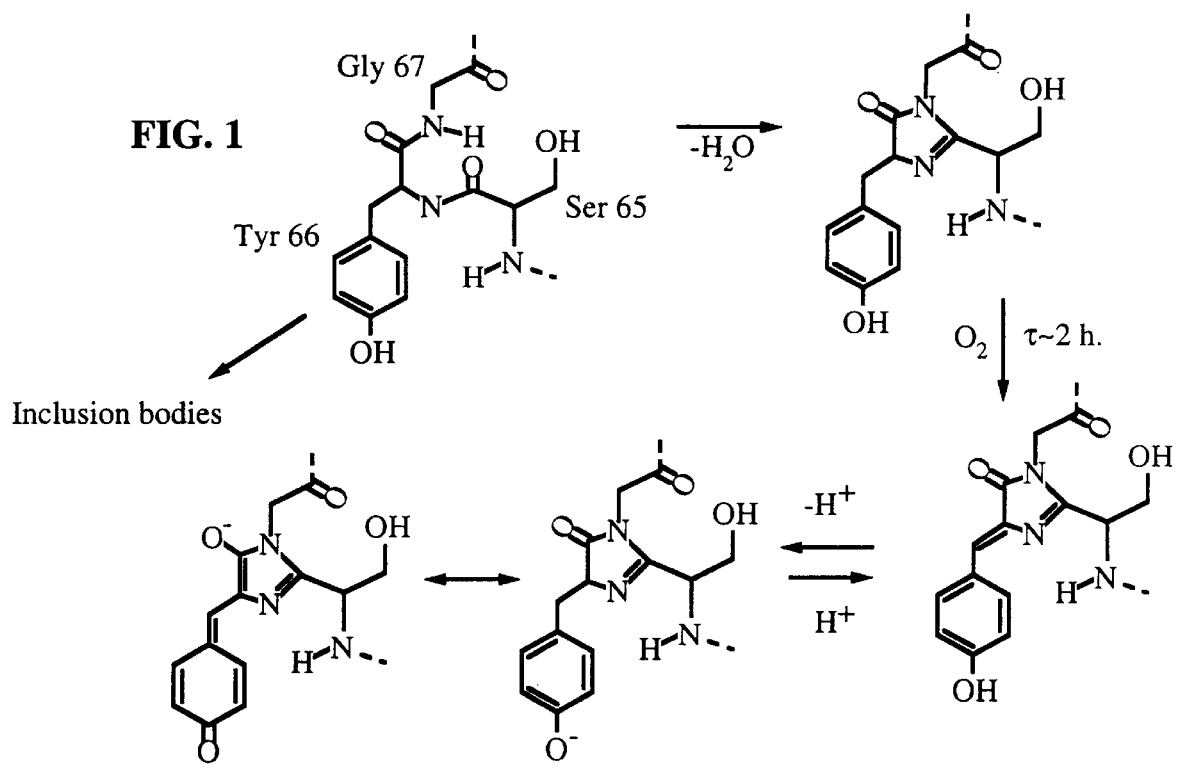
FIG. 1 shows a proposed biosynthetic scheme for the formation of the chromophore of wild-type GFP.

A set of elements is understood to contain one or more elements. The statement that a set of mutations of a protein consists essentially of a given mutation is understood to mean that the set consists of the given mutation and possibly of any other mutations that do not significantly alter the function (spectral properties, brightness) of the protein; any protein in such a set has substantially identical properties to a protein having only the given mutation. The numbering of amino acids in the following description is understood to refer to correspondences with the generally accepted numbering of wild-type GFP; that is, the amino acid at position N of a mutant protein is understood to correspond to the amino acid at position N of wtGFP, and is not necessarily the Nth amino acid of the mutant protein. A target mutagenesis region is understood to refer to a set of amino acids that are mutagenized. The statement that a regulatory element is operatively connected to a coding portion is understood to mean that the regulatory element influences the expression of the coding portion. The present invention is understood to encompass proteins, nucleic acids, and/or cells that are in some way engineered; it is understood to exclude naturally occuring Aequorea cells having undergone no modification. Examples of engineered cells or nucleic acids include non-Aequorea cells and nucleic acids having a non-Aequorea regulatory element.

The following are some of the abbreviations used in the ensuing description: A, absorbance (1 cm); aa, amino acid (s); Ap, ampicillin; bp, base pair(s); FITC, fluorescein isothiocyanate; FACS, fluorescence activated cell sorting; GFP, green fluorescent protein; gfp, gene encoding GFP; IPTG, isopropyl-β-D-thiogalactopyranoside; K, the nucleotide G or T; kb, kilobase(s) or 1000 bp; N, the nucleotide A, T, C or G; nt, nucleotide(s); PBS, phosphate buffered saline; PCR, polymerase chain reaction; oligo, oligodeoxyribonucleotide; wt, wild-type.

GFPs of the present invention were obtained by constructing a library of gfp mutants containing an average of two mutated codons in a target mutagenesis region of 20 codons containing the chromophore, and then selecting the brightly-fluorescing strains by FACS.

Generation of a Library of GFP Mutants

GFP mutants were generated by targeting for mutagenesis aa 55 to 74, the twenty aa immediately surrounding the chromophore and centered around the chromophore. A codon-based mutagenesis scheme was used, as described in more detail in articles by Cormack and Struhl in Science 262 (1993), p. 244–248 and Glaser et al. in J. Immunol. 149 (1992) 3903–3913.

In standard oligonucleotide-directed mutagenesis schemes, defined amounts of the three non-wild-type nucleotides are included at each step of oligonucleotide synthesis. This doping results in a defined mutation rate per nucleotide position, and an equal frequency of the three possible nucleotide substitutions. There is, however, a strong bias at the amino acid level in favor of those substitutions corresponding to codons that differ by a single nucleotide from the wild-type codon.

For a codon-directed mutagenesis scheme there is a certain probability that a particular codon is mutated, but if so there is an equal probability of substituting any of the 32 possible NNK (K=G or T) codons. As a result, the method produces a highly compact yet representative library of mutants. For example, in the region mutagenized in this study, all possible single amino acid changes are covered in approximately 2400 clones.

Figure 2:
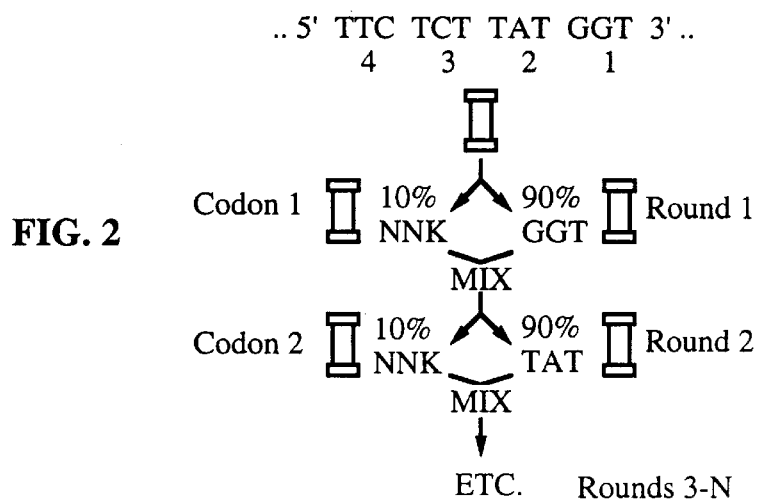
FIG. 2 is a schematic diagram of a codon-based mutagenesis method used to generate mutants of the present invention.

FIG. 2 shows an outline of a codon-directed mutagenesis scheme, with four codons arbitrarily numbered 1–4 used as an example. Codons 1–4 are part of the DNA sequence encoding wild-type protein. The DNA is synthesized by well-known solid-phase methods. Briefly, at the step in oligonucleotide synthesis corresponding to a given codon, the synthesis column is dismantled and the silica matrix is split into two portions and repacked into two synthesis columns. One column is subjected to three rounds of synthesis with the wild-type nucleotides; the second column is subjected to three rounds of synthesis yielding the codon NNK, where N corresponds to an equimolar mix of the four nucleotides, and K to an equimolar mix of G and T. The matrix in the columns is combined and the process repeated for each codon being mutated. The use of only G or T (and not A or C) for the last codon nucleotide does not lead to significant loss of generality for the method, as can be seen from a cursory inspection of the genetic code, shown in Table 2. The codon pairs for which the coded amino acid changes as a result of a substitution of G for A or T for C in the third position are marked by *.

TABLE 2

| First position (5' end) | Second position | | | | Third pos. (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop | Stop* | A |
| | Leu | Ser | Stop | Trp* | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile* | Thr | Lys | Arg | A |
| | Met* | Thr | Lys | Arg | G |
| G | Val | Ala | Asp | Gly | T |
| | Val | Ala | Asp | Gly | C |
| | Val | Ala | Glu | Gly | A |
| | Val | Ala | Glu | Gly | G |

For each codon, 10% of the total silica matrix received the NNK codon, yielding an average of two mutated codons per molecule. Thus, the mutagenesis scheme used was targeted at detecting GFPs with 1–3 mutated residues. Clearly, for a given length of a DNA fragment subject to mutation, the probability of mutating a codon can be varied in order to change the average number of mutated codons per fragment. Thus, mutagenesis schemes similar to the one described above can be used to generate various other mutants.

Selection of Brightly Fluorescing Mutants

To generate mutants of the present invention, a large number of mutants were produced, and the most highly fluorescent mutants were isolated using FACS. A library of $6 \times 10^6$ mutant genes transcribed from a tightly regulated isopropyl-β-D-thiogalactopyranoside (IPTG) inducible promoter was constructed in E. coli. In log phase, in the absence of inducer, the pool of mutants showed negligible fluorescence (data not shown). After induction of log phase cells for 2.5 hours, there was a clear increase in fluorescence for a subpopulation of the library. The result of a FACS scan of the total library 2.5 hours after induction is shown in FIG. 3-A. The horizontal axis shows fluorescence intensity recorded along the direction of excitation, while the vertical axis shows particle size/density recorded as orthogonal light scatter. The non-fluorescing portion of the library is likely to contain non-fluorescing mutants of GFP.

After 2.5 hours of induction with IPTG, FACS was used to isolate the most fluorescent members of the population. FIG. 3-B shows the results a FACS scan of a high-fluorescing subpopulation of the library, after amplification of the subpopulation in broth and induction with IPTG. The most intensely fluorescing 0.5% of this already enriched population was recovered, and 50 of the strains were analyzed in detail. After induction, individual bacterial strains fluoresced between 10- and 110-fold more intensely than a control strain expressing wild-type GFP. FIG. 3-C is a histogram of the number of cells as a function of fluorescence intensity for a wild-type GFP strain and an enhanced-GFP strain excited at 488 nm, with and without induction with IPTG. The integral mean fluorescent intensities were X=2.835 for the wt GFP strain in the presence of IPTG, and X=186.1 for the mutant strain in the presence of IPTG.

The increase in fluorescence intensity for the mutants does not depend on the bacterial strain used, since identical increases in fluorescence intensity were seen when mutant the mutant GFPs were expressed in *E. coli* strains XA90 or DH12S, in *Yersinia pseudotuberculosis,* or in *Salmonella typhimurium* (data not shown). Furthermore, the observed increase in fluorescence is not an artifact of the particular expression system used since the mutant GFPs all resulted in more intense fluorescence than wt GFP when expressed from a T7 promoter.

Characterization of the mutants

The genes corresponding to the 12 most fluorescent isolates were sequenced, and three classes of mutants could be distinguished. Table 3 shows the codons and corresponding residues 64–72 for wild-type GFP, and the mutated codons and corresponding residues for the three classes of mutants.

within one hour the bacteria fluoresce approximately 100-fold more intensely than those expressing wild-type protein.

The dramatic difference in fluorescence between wild-type and mutant strains could in principle be due to any of a number of factors: increased protein expression, more efficient protein folding, increased absorption at 488 nm ($A_{488\ nm}$), or faster chromophore formation. Sequencing of the promoter revealed no mutations for any of the plasmids carrying the mutant GFP, and after induction with IPTG the amount of protein produced by the wild-type and mutant strains was the same. There is, however, a significant effect of the mutations on protein folding. Consistent with what has been previously observed (Heim et al., 1994), we found that much of the wild-type GFP is found in inclusion bodies as non-fluorescent insoluble protein (data not shown). By contrast, when expressed under identical conditions, 90% of GFPmut1 and virtually all of GFPmut2 and GFPmut3 are soluble (data not shown). The high solubility of the mutant proteins contributes to the increased fluorescence of the bacteria expressing the mutant GFP proteins.

To assess the effect of the mutations on the fluorescence of the protein itself, soluble GFP from the three mutant classes was isolated, and excitation and emission spectra were analyzed using fluorescence spectroscopy. The excitation and emission spectra for wild-type and mutant GFPs were measured on a SPEX fluorolog fluorimeter using 1.0 nm bandwidths, and corrected using standard correction files supplied by the manufacturer. The wild-type and mutant

TABLE 3

| Position | 64 | 65 | 66 | 67 | 68 | 69 | 70 | 71 | 72 |
|---|---|---|---|---|---|---|---|---|---|
| GFP wt | TTC<br>Phe | TCT<br>Ser | TAT<br>Tyr | GGT<br>Gly | GTT<br>Val | CAA<br>Gln | TGC<br>Cys | TTT<br>Phe | TCA<br>Ser |
| GFPmut1 | CTG<br>Leu | ACT<br>Thr | | | | | | | |
| GFPmut2 | | GCG<br>Ala | | | CTT<br>Leu | | | | GCG<br>Ala |
| GFPmut3a | | GGG<br>Gly | | | | | | | GCG<br>Ala |
| GFPmut3b | | GGT<br>Gly | | | | | | | GCG<br>Ala |

In was thus determined that positions 64, 68 and 72 are significant potential mutagenesis targets for generating brightly fluorescing GFPs. Previous mutagenesis schemes have unveiled two categories of positions affecting GFP brightness: positions within the chromophore (65 and 66), and linearly far away from the chromophore, although potentially close to the chromophore in the three-dimensional structure of GFP (167, 202, 203). It can be seen from Table 3 that positions linearly close to the chromophore, but outside the chromophore, can be important in generating GFP mutants with improved characteristics.

Figure 4:
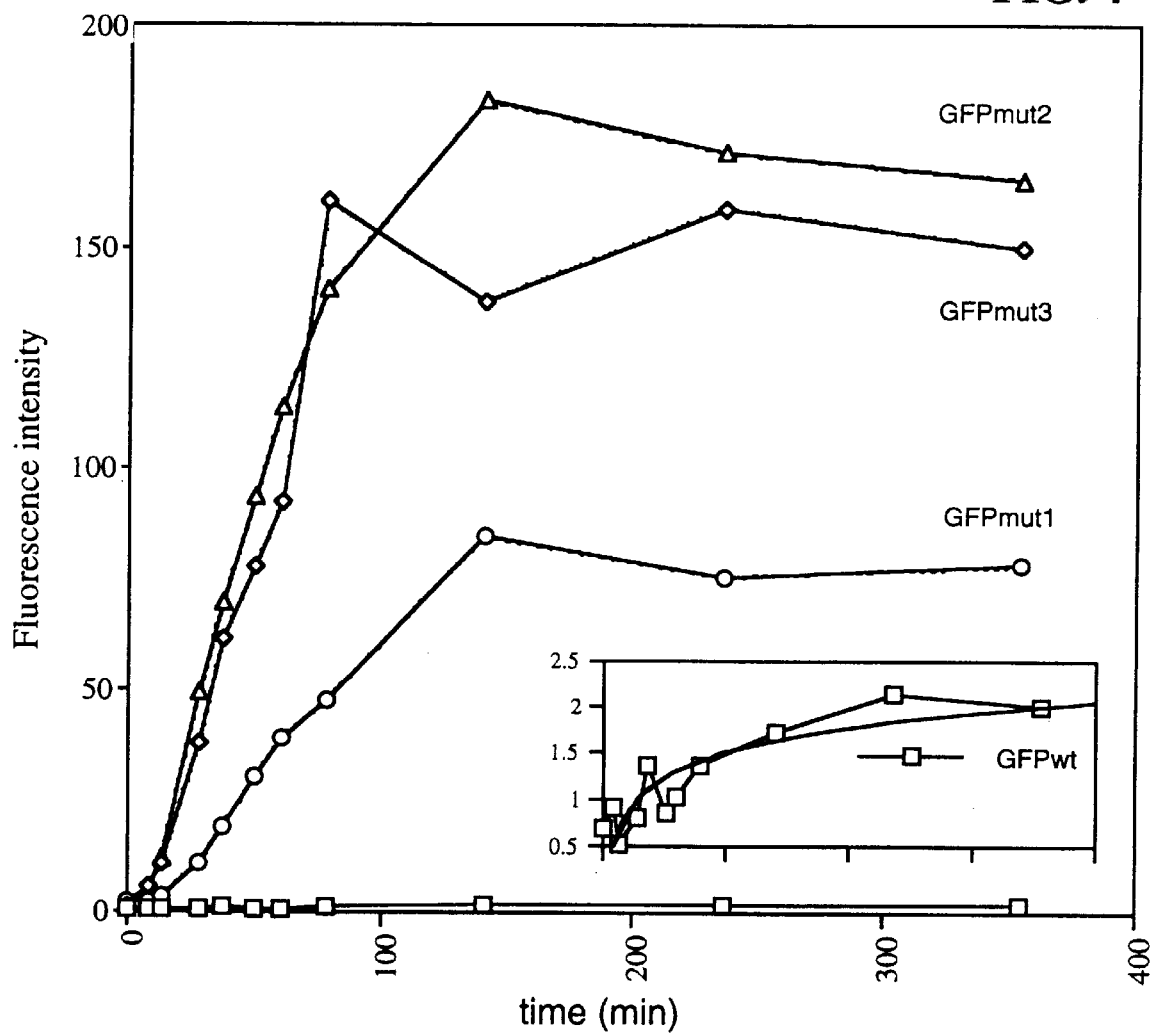
FIG. 4 is a graph of 488 nm-excited fluorescence intensities of three mutants of the present invention and of wild-type GFP, as a function of time after induction.

GFPmut1 has a double substitution: F64L, S65T. GFPmut2 has a triple substitution: S65A, V68L, S72A. The class GFPmut3, represented by ten of the twelve mutants, is characterized by the double aa substitution S65G, S72A. Thus, in all three mutant classes Ser65 is mutated and always in the context of another mutation. After induction with IPTG, the bacterial strains expressing the mutant GFPs already show a substantial (3x) increase in fluorescence by the first time point (8 minutes) after induction. FIG. 4 shows the fluorescence intensities of the three mutant strains as a function of time; the wild-type fluorescence is shown in the inset. Half maximal fluorescence appears by 25 minutes, and excitation spectra are shown schematically in FIG. 5-A, while the emission spectra are shown in FIG. 5-B. The spectrum of each GFP type in FIGS. 5-A and 5-B is normalized individually, so the graphs should not be used for comparing intensities between strains. For a comparison of fluorescence intensities, see the data in Table 4. The excitation maxima were, with emission recorded at 540 nm: wt GFP, 395 nm; GFPmut1, 488 nm; GFPmut2, 481 nm; GFPmut3, 501 nm. The emission maxima were, with excitation at 450 nm for the mutant proteins and at 395 nm for the wild-type protein: wt GFP, 508 nm; GFPmut1, 507 nm; GFPmut2, 507 nm; GFPmut3, 511 nm.

All three mutant proteins show a severe shift in peak absorption frequency from 395 nm for wild-type GFP to 480–501 nm for the three mutant proteins. The emission wavelengths are essentially unchanged, and range from 507 to 511 nm. The gross shift in absorption is responsible for most of the increased fluorescence: spectral measurements with equal amounts of soluble GFP show that with excitation at 488 nm, fluorescence per unit soluble GFP is 19- to 35-fold higher for the three mutants than for wild-type GFP. Table 4 shows the wild-type and mutant relative fluorescence intensities per unit soluble protein, for excitation wavelengths of 395 nm and 488 nm. The figures shown are ratios of fluorescence intensity for each GFP strain to wild-type, for the given excitation wavelength.

TABLE 4

| Excitation Wavelength | 395 nm | 488 nm |
|---|---|---|
| GFP wt | =1 | =1 |
| GFPmut1 | .8 | 35 |
| GFPmut2 | .5 | 19 |
| GFPmut3 | .2 | 21 |

Interestingly, bacteria expressing mutants 2 and 3 fluoresce with more than twice the intensity of those expressing mutant 1, as shown in FIG. 4. Yet, the fluorescence per unit of soluble protein for mutants 2 and 3 is approximately half of that for mutant 1, as shown in Table 4. The difference is partially due to the folding characteristics of the three mutant proteins, since some GFPmut1 protein is found in inclusion bodies, whereas all of GFPmut2 or GFPmut3 is soluble. The increase in fluorescence seen in bacteria expressing the mutants 1–3 is thus largely due to a shift in absorption spectra, and in addition to an increase in soluble protein due to more efficient protein folding.

Previous mutagenesis of GFP has revealed two broad classes of mutants: those with shifts in emission maximum, such as the blue-fluorescing (458 nm) Tyr66Trp shown in Table 1; and those with shifts in excitation maximum, typically to about 490 nm, such as those having Ser65 mutated to Ala, Gly, Ile, Thr or Cys, described in Heim et al. (1995) and Delagrave et al. The mutants of the present invention are related to those in the second class. As shown in Table 3, three independent mutants with substitutions of Ala or Gly for Ser65 were isolated. These substitutions were invariably accompanied by a second substitution, S72A. The double amino acid combination of S65G and S72A is present in the library at a theoretical frequency of 1 in $3.6 \times 10^5$ clones. The fact that this double amino acid substitution was isolated at least twice strongly suggests that the substitutions at both amino acid positions are important for maximal fluorescence. Likewise, while S65T results in a fluorescence intensity increase of six fold over wild type (as disclosed in Heim et al., 1995), (S65T, F64L) (GFPmut1) results in a thirty fold intensity increase over wild-type, as shown in Table 4. Thus a second mutation besides that of Ser65 is critical for maximal fluorescence. The additional mutation(s) may be necessary for efficient folding or chromophore formation; alternatively, they may have a more direct effect on absorption efficiency.

Making and Using Mutants of the Present Invention

DNA encoding wtGFP is available commercially, for example from Clontech in Palo Alto, Calif. Methods of producing mutants containing a predetermined nucleotide sequence are well-known in the art. Two widely-used methods are Kunkel mutagenesis and PCR mutagenesis. A detailed description of the two techniques can be found in *Current Protocols in Molecular Biology*, Wiley Interscience, 1987, Sections 8.1 and 8.5 respectively. Kunkel mutagenesis is also described in an article by Kunkel in *Proc. Acad. Nat. Sci. USA* 82, p.488–492, while PCR is discussed in an article by Saiki et al. in *Science* 239, p.487–491. It is also possible to synthesize mutant GFPs and DNA encoding for mutant GFPs directly, by synthetic methods well known in the art.

The mutant sequences can be expressed in a variety of systems, including bacterial, yeast, plant and mammalian cells. DNA encoding the mutant GFP is inserted in an expression vector and transformed into cells of interest. The sequence encoding for GFP is inserted in the vector in the correct reading frame near a strong promoter, and the expression of gfp is induced. Vectors suitable for specific expression systems are well-known in the art, and are widely available commercially. Vectors having codons optimized for expression in a variety of systems, including yeast and mammalian cells, are also available. For a description of silent nucleotide sequence mutations optimized for mammalian expression, see for example the article by Haas et al. in *Curr. Biol.* 6(3):315–324 (1996).

Mutant GFPs of the present invention are useful in a wide variety of applications, including the monitoring of gene expression and protein localization. Examples of such applications are discussed in some of the papers mentioned in the background section.

Mutant gfps of the present invention are suitable for use as markers for transformation of mammalian cells. Often, a gene of therapeutic interest does not produce an easily distinguishable phenotype in cells expressing that gene. Thus, such a therapeutic gene is usually inserted into a vector that contains a marker gene. The therapeutic gene and the marker gene are placed in the vector under the control of a cellular or viral promoter, and introduced into mammalian cells of interest; subsequently, the transfected cells (the cells containing the vector) are selected according to the phenotype determined by the marker gene. The use of GFP for selection obviates the need to grow the mammalian cells of interest in the presence of drugs in order to select for the transfected cells. Cells transfected with a vector containing gfp and the gene of therapeutic interest are recognized by their fluorescence following 488 nm excitation, and are sorted by FACS.

In another application, a mutant GFP of the present invention is used to select specific cell lines in which expression vectors have integrated at a chromosomal location giving very high expression of GFP and of a second gene. A GFP expression vector is transfected into mammalian cells along with a vector expressing a gene of interest. The two vectors become integrated into the chromosome together, and selection of brightly-fluorescing cells will yield the cells with high levels of expression of the gene of interest.

For the study of protein localization, concatenation of a mutant gfp of the present invention and a gene of interest encoding for a cellular protein, and subsequent expression of the two genes, results in a fluorescent fusion protein that is localized at the normal intracellular location of the protein encoded by the gene of interest. Identifying the intracellular location of the mutant GFP thus identifies the intracellular location of the protein of interest. The use of such fusion proteins yields information on the normal cellular role of the protein encoded by the gene of interest. Such an application using wt GFP is described in more detail, for example, in an article by Olson et al. in *J. Cell Biology*, 130 (1995), p. 639–650. Vectors that can be used for fusing a protein of interest to the N-terminus or the C-terminus of wt GFP are available commercially, for example from Clontech (designations pGFP-N1 and pGFP-C1).

In yet another application, mutants of the present invention are used to select bacterial promoters that are induced in response to a specific stimulus. Such an application allows for the systematic scanning of chromosomes of pathogenic and/or commercially important organisms for genes that are regulated in response to environmental stimuli such as iron starvation, transient stress, and antimicrobial agents. A library of bacterial promoters is created upstream of a gfp mutant of the present invention. The library of promoters is then subjected to the stimulus of interest and the highly fluorescent cells are sorted using FACS. The sorted fraction is then grown in the absence of the stimulus and the sorting process is repeated, selecting out non- or weakly fluorescing cells. Such serial FACS sortings rapidly enrich the fraction of cells having promoter fusions that are up-regulated in response to the given stimulus. This selection technique is particularly useful since sorting can be performed in response to transient and/or complex stimuli, such as those encountered by pathogenic organisms during infection. The selection is fast due to the high processivity of typical flow cytometers, usually on the order of 5000 cells/second. The promoter selection method described above can be used with whole infected mammalian cells, allowing the isolation of genes induced by pathogenic organisms during their intra- cellular life cycle.

For applications using 488 nm excitation, such as those involving typical FACS equipment, the GFP mutants of the present invention hold a clear advantage over wt GFP. Another advantage of the present invention is that the mutants are detectable within minutes of induction in bac- teria growing in log phase at 37° C., while wild-type GFP is not easily detectable until 1–2 hours after induction, under identical conditions.

Pairing mutants with high excitability at 488 nm and low excitability at 395 nm (such as GFPmut1) with complemen- tary mutants having a reduced 470 nm absorption peak and high absorption at 395 nm allows efficient spectral separa- tion of two simultaneously expressed fluorescent tags, one excited specifically at about 395 nm or 370 nm, and the other at 488 nm. Also, because of their novel folding and chro- mophore formation properties, mutant GFPs of the present invention are fluorescent in systems where wild-type GFP has proven to be non- or only weakly-fluorescent.

There are many ways to construct mutants of the present invention. The following examples only illustrate particular ways to obtain and analyze such mutants, and should not be construed to limit the invention.

EXAMPLE 1

To generate a library of mutants, gfp was expressed under control of the tac promoter in pKEN2, a high copy phagemid. The plasmid pKEN2 contains DNA encoding for ampicillin (Ap) resistance. The oligonucleotide GF1, shown below, was used to introduce the ribosome binding site of the phage T7 gene10 upstream of the gfp gene. The sequence of GF1 is: 5' GATTTCTAGA*ATTTAAGAAGGAGATATA- CATATG*AGTAAAGGAGAAG 3' (SEQ ID NO: 5). The coding region of the gfp gene is shown in bold, while the sequence from T7 gene10 is printed in italics. The PstI site at the 5' end of the oligonucleotide was used for cloning. A restriction map of wt gfp is shown in FIG. 6.

The sequence of the mutagenic oligonucleotide GF2 is, with the mutagenized codons in bold and the BglII restric- tion site used for cloning in italics:
5' TG.CTG.TTT.CAT.AAG.ATC.TGG.GTA.TCT-
.TGA.AAA.GCA.TTG.AAC.ACC.AT
A.AGA.GAA.AGT.AGT.GAC.AAG.TGT.TGG.C-
CA.TGG.AAC.AGG.TAG.TTT.TCC.AG T.AGT.GC. 3'
(SEQ ID NO: 6).
Note that the oligonucleotide GF2 is part of the template strand, while the corresponding mutagenized codons shown in Table 3 are part of the coding strand.

The oligonucleotides GF1 and GF2 were used as primers in a PCR amplification of wild-type GFP. PCR was carried out for twenty cycles of 1 minute at 93° C, 3 min at 50° C, and 1 min at 72° C. The amplified fragment was cloned, using the PstI and BglII restriction sites, into a gfp derivative into which a BclI site was introduced at nucleotide 225 (numbering from the ATG). The library is transformed into E. coli strain XA90 ([F'lacI$^{Q1}$ pro AB$^+$] D(lac-pro) XIII ara nal argE(am) thi rif$^R$), an overproducer of lac repressor. In this strain there is very little expression from the tac pro- moter in the absence of inducer.

EXAMPLE 2

For obtaining the FACS scan of FIG. 3-A, the total mutagenized pool was scanned after 2.5 hours of induction. A pool representing $10^6$ independent mutations was diluted 1/100 fold in 2xYT broth (16 g tryptone/10 g yeast extract/5 g NaCl per liter) supplemented with 100 μg/ml ampicillin (Ap) and 0.2 mM IPTG and grown at 37° C. After 2.5 hours the bacterial population was diluted 1/10 in PBS (137 mM NaCl/2.7 mM KCl/4.3 mM $Na_2HPO_{4.7}H_2O$/1.4 mM $KH_2PO_4$) and analyzed in a FACStar$^{Plus}$ (Becton Dickinson) machine equipped with an Ar ion laser emitting at 488 nm. Fluorescence emission was read with a 515/40 band pass filter along the axis of the excitation beam and as orthogonal light scatter. Colinear and side scatter data are collected with logarithmic amplifiers. It was observed that triggering the cell sorter on the side scatter signal led to fewer sorting errors than triggering on the colinear signal.

The results of the scans are graphed as logarithmic contour displays, as shown in FIG. 3-A. The inner bound- aries in the FACS scan (the box in FIG. 3-A) represent the fluorescence channel boundaries (gates) set to sort the mutant population with highest fluorescent intensity. Out of the total number of events, the fraction that fall within the imposed gates were collected and amplified for a second round of selection.

EXAMPLE 3

Strains expressing wt or mutant GFP were grown in 2xYT media to early log phase. The cultures were diluted 1/100 into 2xYT broth supplemented with 100 μg/ml Ap and 0.2 mM IPTG. The dilutions were chosen so that for the entire course of the experiment the bacteria were in log phase. At various times after the addition of inducer, FACS scans were run on the induced cultures as described in Example 2. The time dependence of the fluorescence intensities of strains grown in this manner is shown in FIG. 4. The mean fluorescence of the population was calculated at each time point using the FACS-DESK program. The inset in FIG. 4 shows the average fluorescence of a strain expressing wt GFP, using an expanded Y-axis scale.

EXAMPLE 4

Strains expressing the GFP variants were grown to satu- ration at 30° C. in 2xYT broth supplemented with Ap and 0.2 mM IPTG. At this temperature, GFP from all four strains was more than 90% soluble. GFP was isolated from an equal number of cells for each strain using a french press. The lysate was clarified by spinning at 17,000 g for 30 minutes. The resulting supernatants contained approximately the same amounts of GFP. Equal amounts of GFP, as determined by densitometry of SDS-PAGE gels stained with Coomassie blue, were used to obtain spectra for each strain. The results of such spectral measurements are displayed in Table 4.

EXAMPLE 5

To use gfp as a marker of cell transformation, gfp is placed under the control of the early SV40 promoter in the eucaryotic expression vector pSG5, available commercially from Stratagene. The vector pSG5 contains a sequence encoding for Ap resistance, several restriction sites, and a polyadenylation signal, among others. The early SV40 promoter drives expression of any gene cloned into the vector. The vector containing the mutant gfp of the present invention is then introduced into mammalian cells. For more details on the transfection step see for example the above-mentioned *Current Protocols in Molecular Biology*, Sections 9.1–9.5.

It will be clear to one skilled in the art that the above embodiment may be altered in many ways without departing from the scope of the invention. For example, mutagenesis techniques other than PCR mutagenesis can be used; many plasmids can be used as carriers of gfp; and a variety of expression systems can be chosen. Moreover, many modifications can be made to the GFP mutants disclosed; such modifications include mutations of residues not involved in fluorescence, deletion of non-essential residues, and the addition of residues at a protein end. Various degenerate codons can be used to generate proteins of the present invention. Furthermore, additional mutations can be added to the mutations of the present invention to generate improved GFP strains. Additional mutation positions can also be used in conjunction with mutation positions of the present invention to generate GFPs with desired properties. Accordingly, the scope of the invention should be determined by the following claims and their legal equivalents.

What is claimed is:

1. A mutant *Aequorea victoria* green fluorescent protein, brighter than a wild-type *Aequorea victoria* green fluorescent protein upon 488 nm excitation, wherein a set of mutation positions of said mutant protein comprises position 72.

2. The mutant protein of claim 1, wherein said set of mutation positions further comprises position 65.

3. The mutant protein of claim 1, wherein said set of mutation positions further comprises position 68.

4. The mutant protein of claim 1, wherein said set of mutation positions further comprises position 65 and 68.

5. The mutant protein of claim 1, wherein a set of mutations of said mutant protein comprises a S72A mutation.

6. The mutant protein of claim 5, wherein said set of mutations further comprises a S65A mutation.

7. The mutant protein of claim 5, wherein said set of mutations further comprises a V68L mutation.

8. The mutant protein of claim 5, wherein said set of mutations further comprises a S65A mutation and a V68L mutation.

9. The mutant protein of claim 5, wherein said set of mutations further comprises a S65G mutation.

10. The mutant protein of claim 1, wherein said mutant protein comprises the amino acid sequence as set forth in SEQ ID NO:2.

11. The mutant protein of claim 1, wherein said mutant protein comprises the amino acid sequence as set forth in SEQ ID NO:3.

12. The mutant protein of claim 1, wherein said mutant protein is more soluble than said wild-type protein at 37° C.

13. A mutant green fluorescent protein brighter than a wild-type *Aequoria victoria* green fluorescent protein upon 488 nm excitation, wherein a set of mutations of said mutant protein comprises a F64L and a S65T mutation.

14. The mutant protein of claim 13, wherein said mutant protein comprises the amino acid sequence as set forth in SEQ ID NO:1.

15. The mutant protein of claim 13, wherein said mutant protein is more soluble than said wild-type protein at 37° C.

* * * * *